United States Patent [19]

Bottelberghe et al.

[11] Patent Number: 5,288,879

[45] Date of Patent: Feb. 22, 1994

[54] TETRAHALOPHTHALIC ANHYDRIDE PROCESS

[75] Inventors: Scott A. Bottelberghe, Waldo; Bonnie G. McKinnie, Magnolia; Steven G. Miller, Magnolia; David E. Raposa, Magnolia, all of Ark.

[73] Assignee: Ethyl Corporation, Richmond, Va.

[21] Appl. No.: 952,693

[22] Filed: Sep. 28, 1992

[51] Int. Cl.$^5$ ............................................. C07D 307/89
[52] U.S. Cl. ..................................................... 549/246
[58] Field of Search ......................................... 549/246

[56] References Cited

U.S. PATENT DOCUMENTS 3,382,254  5/1968  Jenkner et al. ....................... 549/246
4,785,121 11/1988  Leone-Bay et al. ................. 549/246
5,059,697 10/1991  Fertel et al. ........................... 549/246

Primary Examiner—Emily Bernhardt
Attorney, Agent, or Firm—David E. LaRose

[57] ABSTRACT

This invention relates to an improvement in a process for preparing tetrabromophthalic anhydride whereby there is a substantial recovery of reactants such as halogen and SO$_3$ from a vent stream exiting the reaction vessel. The improvement comprises contacting the vent stream with a fluid having a first oleum concentration and recovering a halogen stream and a second stream, having a second oleum concentration wherein the second oleum concentration is greater than the first oleum concentration.

23 Claims, 1 Drawing Sheet

TETRAHALOPHTHALIC ANHYDRIDE PROCESS

BACKGROUND

This invention relates to an improvement in a process for preparing tetrahalophthalic anhydride whereby there is a substantial recovery of reactants and by-products such as halogen, $SO_3$, and $SO_2$, from a vent stream exiting the reaction vessel.

Methods for the formation of tetrahalophthalic anhydride, particularly tetrabromophthalic anhydride and tetrachlorphthalic anhydride are well known. A widely used method for halogenating phthalic anhydride is disclosed by Jenkner et al. U.S. Pat. No. 3,382,254 wherein bromine is reacted with phthalic anhydride in a molar ratio of 2.01 to 2.1 at temperatures of 80° to 110° C. in the presence of a small quantity of halogenation catalyst and 4.4 to 4.8 moles of sulfur trioxide in the form of 50 to 80% oleum per mole of phthalic anhydride. After completion of the addition of bromine, the excess sulfur trioxide and bromine are distilled off from the reaction mixture by heating the reaction mixture to 130° to 145° C.

While a considerable amount of the sulfur trioxide and bromine distilled from the reaction vessel can be condensed and recycled to the reaction vessel, there remains a non-condensible stream containing a substantial amount of bromine and $SO_3$ which cannot be economically recovered by conventional techniques. Since $SO_3$ has such a high melting point, solid $SO_3$ forms readily upon cooling the vent stream, thus making separation and handling of the vent stream more difficult. Until now, neutralization of this non-condensable reaction vent stream has been the only viable means for removing substantially all of the $SO_3$ and bromine before discharging the vent stream to the atmosphere.

Thus an object of this invention is to provide a facile economic means for removing essentially all of the residual halogen and $SO_3$ in the reactor vent stream before exhausting the vent stream to the atmosphere. Another object of this invention is to reduce the amount of purchased oleum by using the recovered $SO_3$ from the reaction vent stream to increase the concentration of oleum in a dilute oleum solution. Other objects of this invention will be evident from the following description and appended claims.

SUMMARY OF THE INVENTION

Accordingly, this invention provides, inter alia, an improvement in a process for preparing halogenated phthalic anhydride in a reaction vessel by reacting phthalic anhydride with halogen in an oleum reaction medium wherein a vent stream from the reaction vessel contains a substantial amount of $SO_3$, $SO_2$, and halogen. The improvement comprises: (a) contacting the reaction vessel vent stream with a fluid having a first oleum concentration, and (b) recovering two liquid streams: one containing a minor amount of halogen and having a second oleum concentration; and the second liquid stream comprising halogen and containing a minor amount of $SO_3$ and $SO_2$, wherein the second oleum concentration is greater than the first oleum concentration and wherein a substantial amount of the $SO_3$ and halogen in the reaction vessel vent stream has been removed.

DETAILED DESCRIPTION

Figure 1:
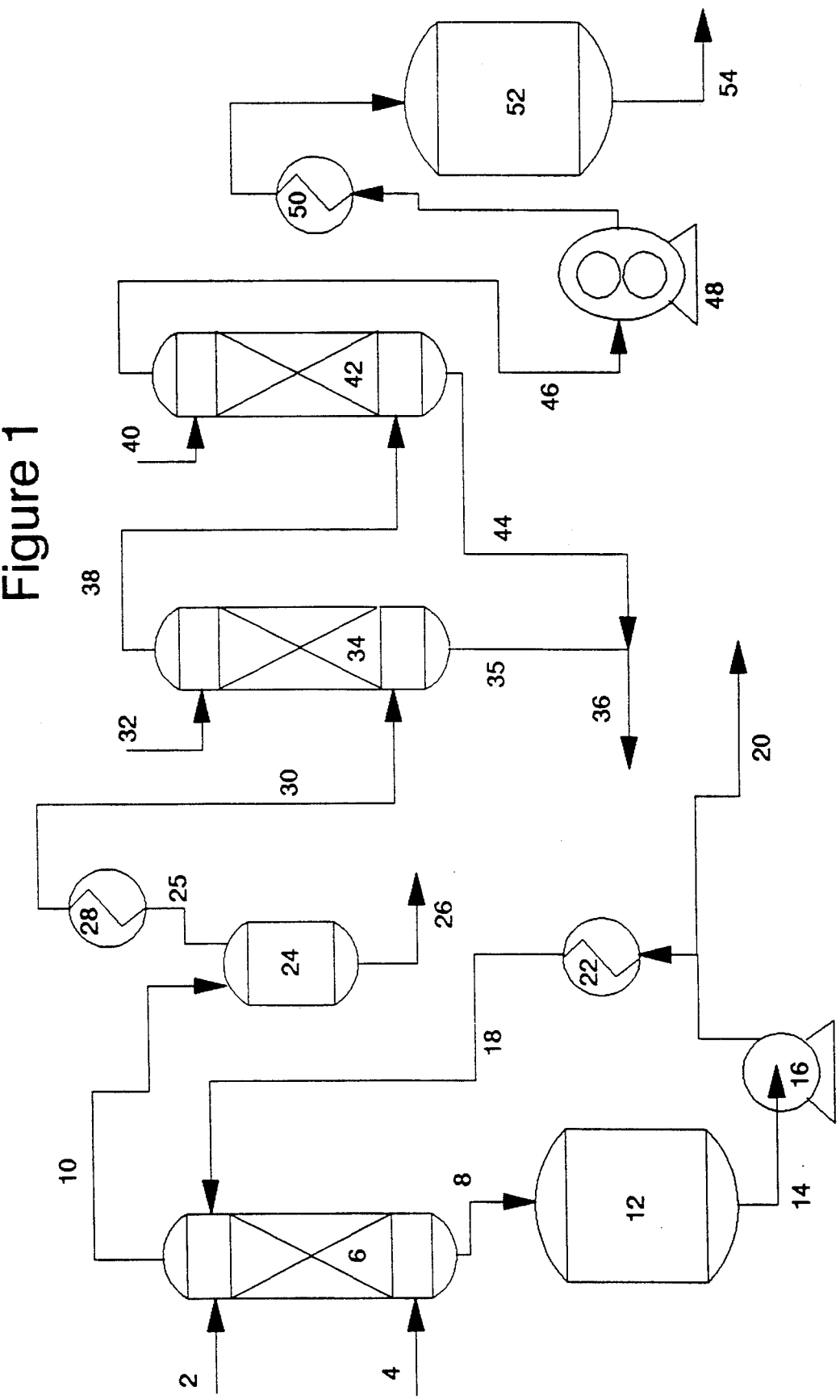
FIG. 1 is an illustration, not to scale, of the process for removal and recovery of $SO_3$, halogen, and $SO_2$ from the vent stream of a tetrahalophthalic reaction vessel.

In the halogenation reaction of phthalic anhydride, the phthalic anhydride is contacted with halogen, preferably bromine, or chlorine, and most preferably bromine, in a reaction vessel containing oleum. Oleum, otherwise known as fuming sulfuric acid, provides an easily stirrable reaction medium for the halogenation reaction as well as oxidizing hydrohalic acid in the reaction medium to halogen. Typically, the oleum used is between 50 and 80 weight percent $SO_3$. Particularly preferred is an oleum concentration of about 65 weight percent $SO_3$ however, this invention is not limited to any particular oleum concentration, provided the oleum concentration is sufficient for the purpose of halogenating the phthalic anhydride.

During the reaction of halogen with phthalic anhydride, one mole of hydrohalic acid is formed per mole of halogen used. The hydrohalic acid thus formed reacts with sulfur trioxide to form halogen, $SO_2$ and water thereby reducing the oleum concentration according to the following reactions

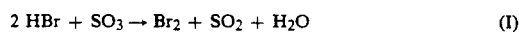

$$2\ HBr + SO_3 \rightarrow Br_2 + SO_2 + H_2O \qquad (I)$$

and

$$H_2O + SO_3 \rightarrow H_2SO_4. \qquad (II)$$

A crystalline halogenated phthalic anhydride product forms during the halogenation reaction. After completion of the halogenation reaction, heat is applied to the reaction mass to distill off $SO_2$, $SO_3$, and excess halogen from the reaction medium, containing the crystalline product. Thus, in addition to the formation of water in the reaction, the concentration of oleum in the reaction medium is further reduced by distillation and venting of $SO_3$. Once sufficient halogen and $SO_3$ have been distilled off, the reaction medium containing the crystalline halogenated product is cooled. The cooled reaction medium is then separated from the reaction medium by centrifugation, decantation, filtration, and the like. Filtrate or centrate separated from the halogenated product having a lower oleum concentration can be reconstituted and recycled to the process.

In general, the oleum concentration after completion of the halogenation reaction and distillation to remove $SO_3$, $SO_2$, and halogen is less than 35 weight percent $SO_3$, more likely, less than 30 weight percent $SO_3$, and most likely, about 25 weight percent $SO_3$ or less. Until now, prior to separating the halogenated product from the reaction medium, the reaction medium was diluted the addition of water from about 22 weight % $SO_3$ to about 95 by the addition of water from about 22 weight % $SO_3$ to about 95 to 98 weight % sulfuric acid. While not desiring to be bound by theory, it was believed that such dilution and disposal of the reaction medium was required due to the impurities in the reactants. It has now been discovered, that filtration from oleum having about 22 weight % $SO_3$, and reconstitution and recycling of a significant amount, but less than 100 weight % of oleum to the reaction vessel, does not adversely affect the purity of the product thus obtained. As an effect of this discovery, the reconstitution of spent oleum which is recycled from the reaction vessel results in a significant savings in operating costs and disposal costs of spent oleum solutions.

This dilute oleum solution recovered as filtrate or centrate from a filter or centrifuge may be reconstituted by the addition of essentially pure $SO_3$. By essentially pure is meant 95 to 99+ weight percent $SO_3$. Preferably, the reconstitution of the dilute oleum stream is coupled with the improvement of this invention thereby providing a facile economic means for increasing oleum concentration while at the same time providing a vent stream which can be exhausted into the atmosphere without increasing the risks to health and the environment.

An important feature of this invention is the step of contacting a reaction vessel vent stream containing $SO_3$ and $SO_2$ halogen with a fluid having a first oleum concentration thereby recovering a more concentrated oleum solution. The contact can be accomplished in any suitable vapor-liquid contact equipment such as an elongated column filled with contact packing, a vessel filled with the contact fluid, and the like. Preferred is a contact vessel, such as a scrubber, filled with packing material resistant to concentrated sulfuric acid, oleum, $SO_3$, and halogen. Such a contact vessel may have any configuration, provided there is sufficient contact between the liquid and vapor streams. Generally an upright elongated column, filled with a suitable amount of contact packing is adequate to achieve the purposes of this invention.

When using an upright elongated contact column, the fluid having the first oleum concentration is fed counter-currently to the reaction vessel vent stream containing $SO_3$, halogen and $SO_2$. Thus when the vent stream is fed into the bottom of the upright elongated column, and the fluid having the first oleum concentration is fed into the top of the column, there is formed a fluid having a second oleum concentration exiting the bottom of the column.

A key feature of this invention is the formation of a fluid having a second oleum concentration wherein the second oleum concentration is greater than the first oleum concentration. As beforementioned, upon completion of the halogenation reaction and distillation to remove $SO_3$, $SO_2$, and excess halogen, the first oleum concentration is typically about 20 to 25 weight percent $SO_3$. Using the improvement of this invention, the second oleum concentration is preferably greater than about 20 weight percent $SO_3$, more preferably greater than about 25 weight percent $SO_3$, and most preferably about 30 to 35 weight percent $SO_3$ or more Exiting the top of the column is an $SO_2$ vapor stream having a reduced amount of $SO_3$ and containing halogen. This $SO_2$ vapor stream may be further contacted with the fluid having a first oleum concentration in a second contact column, if desired, in order to remove additional $SO_3$ from the stream exiting the first contact column.

While not required, it is highly desirable to cool the $SO_2$ vapor stream, containing a reduced amount of $SO_3$ so as to condense at least a portion of the halogen prior to venting the vapor stream to the atmosphere or further treatment to recover $SO_2$ byproduct. Typically, the major portion of halogen initially present in the reaction vent stream is condensed after removal of a substantial amount of $SO_3$ initially present in the reaction vessel vent stream. The condensed halogen stream may contain a minor amount of $SO_3$. By minor amount is meant less than about 20 weight percent $SO_3$. The amount of $SO_2$ in the condensed halogen stream will depend largely on the operating temperature and pressure of the halogen condensor. It is preferred that the halogen stream contain less than 20 weight percent $SO_2$. Most preferably the halogen stream should contain less than about 10 weight percent $SO_2$, and less than 20 weight percent $SO_3$, most preferably less than 15 weight percent $SO_3$.

In another embodiment, the $SO_2$ vapor stream, after contact with the fluid having the first oleum concentration and condensation of a substantial portion of the halogen present, is further treated to recover $SO_2$ as a liquid byproduct. Such further treatment includes scrubbing the $SO_2$ vapor stream with water to remove, any remaining $SO_3$, and halogen, and subsequently drying $SO_2$ vapor stream with 98 weight percent sulfuric acid then compressing and cooling the $SO_2$ to form a liquid $SO_2$ byproduct stream. Thus more than about 75 weight percent, preferably more than about 80 weight percent, and most preferably more than about 90 weight percent of $SO_2$ initially present in the reaction vessel vent stream can be recovered as a saleable byproduct.

In the process of this invention any suitable temperatures and pressures may be used. Thus the pressure may range from subatmospheric to superatmospheric. For the ease of operation, pressures at or slightly above atmospheric are preferably used. The temperature during contact of the fluid having the first oleum concentration with the reaction vessel vent stream should be low enough so that the oleum vapor pressure is below the desired operating pressure during the contacting step in order to increase the amount of $SO_3$ absorbed by the fluid. If the temperature during the contacting step results in the vapor pressure of the oleum being greater than or equal to the desired operating pressure, increased operating pressures may be required to reduce the amount exiting the contact column. Thus the fluid temperature should be below about 58° C., more preferably below about 50° C. and most preferably from about 25° to about 40° C. Temperatures below about 20° C. should be avoided if possible due to the high melting point of $SO_3$ and oleum.

Referring now to FIG. 1, reaction vessel vent stream containing halogen, $SO_3$, and $SO_2$ is fed to the lower portion of upright elongated $SO_3$ absorption column 6 containing contact packing. A filtrate stream 2 having a first oleum concentration is fed to the upper portion of column 6 wherein it contacts stream 4 in a countercurrent manner. Exiting the top of column 6 is a vapor stream 10 containing halogen, $SO_2$, and a reduced amount of $SO_3$. Exiting the bottom of column 6 is a liquid oleum stream 8 containing an increased amount of $SO_3$ and a minor amount of $SO_2$ and halogen This stream is fed to column recirculation tank 12 for recirculation via pump 16 and cooler 22 back to column 6 through recirculation conduit 18. A portion of the liquid oleum stream 14 is removed as product stream 20 which may be further concentrated up to about 65 weight percent $SO_3$ by the addition of 100 weight percent $SO_3$.

Vapor stream 10 is fed to separation vessel 24 wherein a liquid halogen stream 26 containing a minor amount of $SO_3$ and $SO_2$ is obtained for recycle back to the halogenation process. Condenser 28 provides a condensate stream 25 enriched in halogen and an $SO_2$ vapor stream 30 which is fed to halogen scrubbing column 34 wherein essentially all of the halogen and remaining $SO_3$ is removed from stream 30 by contacting the stream counter-currently in column 34 with water 32. Exiting the bottom of column 34 is a liquid stream containing sulfuric acid, HBr, water, and a minor amount of $SO_2$. Purified $SO_2$ vapor stream 38 containing water vapor is then fed to acid drying column 42 wherein the moisture in vapor stream 38 is removed by countercurrently contacting the vapor stream with 98 weight percent sulfuric acid stream 40. Essentially dry $SO_2$ stream 46 is then compressed in compressor 48, cooled in condenser 50 and fed to $SO_2$ storage tank 52 for sale as a liquid $SO_2$ product 54. Dilute acid stream 44 from the bottom of acid drying column 42 is combined with liquid stream 35 exiting the bottom of absorption column 34 to form weak acid stream 36 containing water, $SO_2$, hydrohalic acid and sulfuric acid. This stream may be neutralized or otherwise disposed of.

Utilizing the improvement of this invention, a substantial amount of $SO_3$, and halogen is removed from the reaction vessel vent stream. By substantial amount is meant more than about 40 weight percent of halogen and more than 70 weight percent $SO_3$, more preferably, more than about 45 weight percent halogen and more than 80 weight percent $SO_3$, and most preferably more than about 50 weight percent of halogen and more than about 90 weight percent of $SO_3$ initially present in the vent stream is removed.

A particular advantage of the improvement of this invention is the substantial savings realized by eliminating the neutralization step previously used to treat the reaction vessel vent stream before it was discharged to the atmosphere. Another advantage of this invention is the recovery of useable by-products such as an oleum stream having 30 weight percent or greater $SO_3$, a recycle halogen stream, and the recovery of a purified $SO_2$ stream. Still another advantage is the filtration from oleum having 20 to 25 weight % $SO_3$ rather than from concentrated sulfuric acid, thus avoiding the disposal of a significant amount of sulfuric acid after completion of the bromination reaction.

In order to further illustrate the advantages of this invention the following examples are given. These examples are not meant to limit the invention in any way.

EXAMPLE 1

Filtration from Oleum having 20 wt. % $SO_3$

Phthalic anhydride (59.2 grams, 0.4 moles) and 155 mL (370 grams) of oleum (65 wt. % $SO_3$) were combined in a 500 mL round-bottom flask equipped with an agitator and a Vigreau column which had a $-8°$ C. refrigerated condenser. The phthalic anhydride and oleum mixture was heated to 5° C. and bromine (41 mL) and distillate (85 grams $SO_3$ plus $Br_2$ from a previous reaction) were added slowly over 1.5 hours. The temperature was maintained at 53° to 58° C. during the bromine and distillate addition. The mixture was stirred at 53° to 55° C. for 0.5 hours, then $SO_3$ and $Br_2$ were distilled until the reaction mass temperature was 129° C. In all, 71 grams of distillate ($SO_3$ and $Br_2$) were collected. The reaction mixture was cooled slowly to 60° C., then filtered under reduced pressure (water aspirator) and nitrogen atmosphere through a 25–50 micron glass frit. In about 2 minutes, 130 grams of filtrate was obtained (oleum having 19 wt. % $SO_3$). The filter cake was placed into 600 mL of water, stirred well, water washed, then oven dried. The analysis by vapor phase chromatography (VPC) on a 15 M DB-5 megabore capillary showed the product contained 95.6 area % tetrabromophthalic anhydride, and 4.4 area % tribrominated phthalic anhydride impurities.

EXAMPLE 2

Filtration from Oleum having 20 wt. % $SO_3$

The procedure of Example 1 was repeated using 59.2 grams of phthalic anhydride, 51 mL of $Br_2$, 71 grams of distillate ($SO_3$ and $Br_2$) from Example 1, and 130 grams of filtrate Example 1 which was reconstituted to oleum having 60 wt. % $SO_3$ by the addition of $SO_3$ to give 283 grams of concentrated oleum. The $SO_3$ added was obtained by distilling 65% oleum. Distillate and filtrate were again collected. The dried product which was filtered from oleum (19 wt. % $SO_3$) and purified by washing with water as in Example 1, was analyzed as in Example 1 by VPC. Analysis indicated that the product contained 3.6 wt. % tribrominated phthalic anhydride impurities and 96.3 wt. % tetrabromophthalic anhydride.

EXAMPLE 3

Filtration from Oleum having 20 wt. % $SO_3$

The procedure of Example 1 was repeated using 59.2 grams of phthalic anhydride, 45 mL of $Br_2$, 119 grams of distillate ($SO_3$ and $Br_2$) from Example 2, and 162 grams of filtrate from Example 2 which was reconstituted to oleum having 61 wt. % $SO_3$ by the addition of $SO_3$ to give 332 grams of concentrated oleum. The $SO_3$ added was obtained by distilling 65% oleum. Distillate and fil-trate were again collected. The dried product which was filtered from oleum (19 wt. % $SO_3$) and purified by washing with water as in Example 1, was analyzed as in Examples 1 and 2 by VPC. Analysis indicated that the product contained 2.6 wt. % tribrominated phthalic anhydride impurities and 97.4 wt. % tetrabromophthalic anhydride.

Example 4 illustrates a process for the recovery of $SO_3$, $Br_2$, and $SO_2$ from the reaction vessel vent stream during the distillation of the product after bromination.

EXAMPLE 4

In the production of tetrabromophthalic anhydride, there is formed a reaction vessel vent stream 4 containing $SO_2$ (1779 grams, 27.8 moles), bromine (870 grams, 5.45 moles), and $SO_3$ (928 grams, 11.6 moles) at 25°0 C. and atmospheric pressure. This stream is fed into the bottom of an upright elongated column 6 containing contact packing. A dilute oleum stream 2 from the product filtration containing 20 weight percent $SO_3$ is fed into a post scrubbing column and, subsequently, into the top portion of the upright elongated column 6 wherein it contacts the vent stream 4 in a counter current manner in both the post scrubbing column and the upright elongated column. Exiting the top portion of the post scrubbing column is a vapor stream 10 containing $SO_2$ (1738.5 grams, 27.1 moles), $SO_3$ (103 grams, 1.3 moles), and bromine (823.1 grams, 5.2 moles) at a temperature of about 58° C. This vapor stream is fed into jacketed separation tank 24 wherein a portion of the vapor stream is condensed to form an enriched bromine stream by cooling the separation tank 24 to a temperature of about 13° C. The outlet of separation tank 24 is further cooled to $-4°$ C. by condenser 28. The enriched bromine condensate stream 25 from condenser 28 is collected in separation tank 24. The enriched bromine stream 26 containing bromine (496.6 grams, 3.1 moles), $SO_2$ (59.5 grams, 0.9 moles), and $SO_3$ (86.5 grams, 1.1 moles) is recycled to the bromination process. The non-condensed vapor stream 30 enriched in $SO_2$ (1679 grams, 26.2 moles) and containing a minor amount of bromine (326.5 grams, 2.01 moles) and $SO_3$ (16.5 grams, 0.2 moles) is fed to a scrubbing and drying system for recovery of $SO_2$. Exiting the bottom of upright column 6 is an enriched oleum stream 8 containing 32 weight percent $SO_3$, $SO_2$ (40.5 grams, 0.6 moles), and bromine (46.9 grams, 0.3 moles).

In the $SO_2$ recovery system, vapor stream 30 is fed to absorption column 34 wherein it is contacted with water (1421 grams, 78.9 moles). The water absorbs essentially all of the bromine, and $SO_3$ in the $SO_2$ vapor stream. The absorption column is operated at atmospheric pressure and about 38° C. Exiting the top of the absorption column is a vapor stream 38 containing $SO_2$ (1674 grams, 26.1 moles) and water vapor (34.5 grams, 1.9 moles). This $SO_2$ rich stream is then dried by contacting the stream with 98 weight percent sulfuric acid in an acid drying column 42 at about 38° C.

While the above process is typically conducted as a batch or semi batch operation, the improvement of this invention can be adapted to recovery of $SO_3$ and halogen on a continuous basis. Other variations of the present invention are within the spirit and scope of the appended claims.

What is claimed is:

1. In a process for preparing a halogenated phthalic anhydride product in a reaction vessel by reacting phthalic anhydride with halogen in an oleum reaction medium wherein a vent stream from the reaction vessel contains a substantial amount of $SO_3$, $SO_2$, and halogen, wherein the halogen is selected from the group consisting essentially of bromine and chlorine, the improvement comprising:
   a) contacting the reaction vessel vent stream with a fluid having a first oleum concentration, and
   b) recovering two liquid streams: (i) one containing minor amounts of halogen and having a second oleum concentration; and (ii) a second liquid stream comprising halogen and containing a minor amount of $SO_3$ and $SO_2$, wherein the second oleum concentration is greater than the first oleum concentration and wherein a substantial amount of the $SO_3$, $SO_2$, and halogen in the reaction vessel vent stream has been recovered.

2. The improvement of claim 1 wherein the halogen is bromine.

3. The improvement of claim 2 wherein the amount of bromine recovered is greater than about 50 percent based on the initial weight of bromine in the reaction vessel vent stream.

4. The improvement of claim 3 wherein the amount of $SO_3$ recovered is greater than about 90 percent based on the initial weight of $SO_3$ in the reaction vessel vent stream.

5. The improvement of claim 1 wherein the amount of halogen recovered is greater than about 50 percent based on the initial weight of halogen in the reaction vessel vent stream.

6. The improvement of claim 1 wherein the amount of $SO_3$ recovered is greater than about 90 percent based on the initial weight of $SO_3$ in the reaction vessel vent stream.

7. The improvement of claim 1 wherein the first oleum concentration is about 25 weight percent $SO_3$ or less.

8. The improvement of claim 1 wherein the second oleum concentration is greater than about 30 weight percent $SO_3$.

9. The improvement of claim 4 wherein the first oleum concentration is about 25 weight percent $SO_3$ or less.

10. The improvement of claim 9 wherein the second oleum concentration is greater than about 30 weight percent $SO_3$.

11. The improvement of claim 10 further comprising recovering a substantial amount of $SO_2$ from the reaction vessel vent stream.

12. The improvement of claim 11 wherein the amount of $SO_2$ recovered is greater than about 90 weight percent based on the initial weight of $SO_2$ in the reaction vessel vent stream.

13. The improvement of claim 1 further comprising recovering a substantial amount of $SO_2$ from the reaction vessel vent stream.

14. The improvement of claim 13 wherein the amount of $SO_2$ recovered is greater than about 90 weight percent based on the initial weight of $SO_2$ in the reaction vessel vent stream.

15. The improvement of claim 1 wherein the fluid having a first oleum concentration is formed by filtering the halogenated phthalic anhydride product from a reaction mixture without first diluting the reaction mixture to form concentrated sulfuric acid.

16. The improvement of claim 12 wherein the fluid having a first oleum concentration is formed by filtering the halogenated phthalic anhydride product from a reaction mixture without first diluting the reaction mixture to form concentrated sulfuric acid.

17. In a process for preparing a brominated phthalic anhydride product in a reaction vessel by reacting phthalic anhydride with bromine in an oleum reaction medium whereby a reaction vessel vent stream containing a substantial amount of $SO_3$, $SO_2$, and bromine is present, the improvement comprising:
   a) filtering the brominated phthalic anhydride product from a reaction mass without diluting the reaction mass with water thereby forming a filtrate with a first oleum concentration;
   b) contacting the reaction vessel vent stream with the filtrate having a first oleum concentration; and
   c) recovering a first stream containing bromine and a minor amount of $SO_3$, and a second stream having a second oleum concentration, wherein the second oleum concentration is greater than the first oleum concentration and wherein a substantial amount of the $SO_3$ and halogen initially present in the reaction vessel vent stream has been recovered.

18. The improvement of claim 17 wherein the amount of bromine recovered is greater than 50 percent based on the initial weight of bromine in the reaction vessel vent stream.

19. The improvement of claim 17 wherein the amount of $SO_3$ recovered is greater than about 90 percent based on the initial weight of $SO_3$ in the reaction vessel vent stream.

20. The improvement of claim 17 wherein the first oleum concentration in the filtrate is about 25 weight percent $SO_3$ or less.

21. The improvement of claim 19 wherein the second oleum concentration is greater than about 30 weight percent $SO_3$.

22. The improvement of claim 21 further comprising recovering a substantial amount of $SO_2$ from the reaction vessel vent stream.

23. The improvement of claim 22, wherein the amount of $SO_2$ recovered is greater than about 90 weight percent based on the initial weight of $SO_2$ in the reaction vessel vent stream.

* * * * *